| United States Patent [19] | [11] Patent Number: 4,659,664 |
| de Buda | [45] Date of Patent: Apr. 21, 1987 |

[54] STRUCTURES CONTAINING IMMOBILIZED MICROBIAL CELLS

[75] Inventor: Francis de Buda, Santa Barbara, Calif.

[73] Assignee: Excel-Mineral Company, Inc., Goleta, Calif.

[21] Appl. No.: 732,685

[22] Filed: May 10, 1985

[51] Int. Cl.$^4$ .................. C12N 11/14; C12N 11/10; C12N 11/12; C12N 11/04
[52] U.S. Cl. .................. 435/176; 435/178; 435/179; 435/182
[58] Field of Search ............... 435/174, 176, 177, 178, 435/179, 180, 181, 182

[56] References Cited

U.S. PATENT DOCUMENTS

| 3,791,927 | 2/1974 | Forgione et al. | 435/182 |
| 4,169,014 | 9/1979 | Goldberg | 435/182 |
| 4,226,938 | 10/1980 | Yoshida et al. | 435/176 |
| 4,272,617 | 6/1981 | Kaetsu et al. | 435/182 |
| 4,391,909 | 7/1983 | Lim | 435/182 X |

*Primary Examiner*—David M. Naff
*Attorney, Agent, or Firm*—Edward D. O'Brian

[57] ABSTRACT

The strength of a bead containing microbial cells within a retaining permeable membrane is improved by incorporating finely divided sericitic clay particles within a hydrocolloid-containing composition used to form the membrane. The hydrocolloid is preferably alginic acid, carboxymethyl cellulose, methylethylcellulose or polyvinyl alcohol in an amount of about 10 to 40% by weight.

4 Claims, 1 Drawing Figure

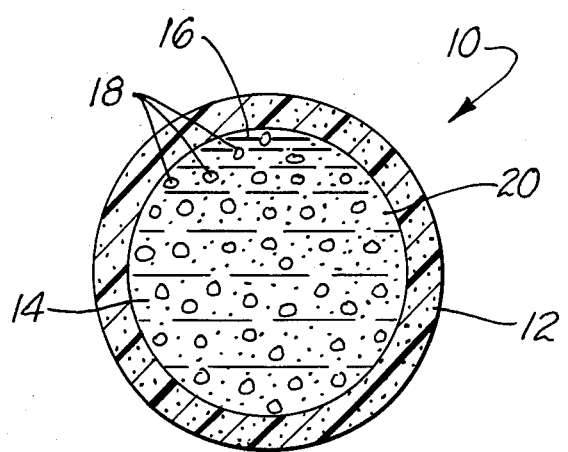

STRUCTURES CONTAINING IMMOBILIZED MICROBIAL CELLS

This invention pertains to new and improved structures containing immobilized microbial cells. Structures of this type are primarily useful in various types of bioreactors which utilize cell endo or fixed enzymes associated with such cells to cause one or more chemical reactions or transformations.

A number of different structures have been utilized for the purpose of holding or immobilizing eukaryote microbial cells containing endo or fixed enzymes as such cells are contacted by an appropriate solution so that enzyme caused reactions or transformations will take place as the nutrient solutions are supplied to the cells and as one or more reaction products are removed from them. The present invention is primarily concerned with structures of this category in which the microbial cells are held within sphere-like beads. Occasionally such beads are referred to simply as spheres or as bioreactor spheres. Occasionally they are referred to as cell containing spheres and occasionally they are referred to as beads or spheres utilizing a membrane to retain cells within the interiors of these structures.

Such beads or spheres containing microbial cells can be manufactured in several different manners. It is considered that they are most commonly created by forming a mixture in which the microbial cells are mixed with a solution containing at least one hydrocolloid and then contacting small amounts or drops of the mixture with an appropriate reagent(s) or ion(s) capable of rendering the exteriors of such bodies substantially insoluble by the formation of a permeable barrier layer, film or membrane. Such a barrier or membrane serves to hold the cells in place within the membrane. If desired the mixture within the membrane may be formulated so that it will become of a gel or gel-like character.

Perhaps this latter should be explained by indicating one particular process which has previously been used in creating bioreactor beads or spheres as briefly indicated in the preceding discussion. Such structures have been created by mixing cells containing enzymes desired for one or more specific, intended reactions or transformations into an aqueous sodium alginate solution, then forming this mixture into small drops or spheres and then finally contacting the external surfaces of the latter with an aqueous solution containing the calcium ion for a time and at a temperature sufficient so as to form a calcium alginate film or membrane around each such sphere or bead.

This generalized type of process is recognized as being capable of being utilized with other hydrocolloid or hydrocolloid type of materials than alginic acid or a soluble salt of this acid. It is not considered necessary in this specification to list various natural plant hydrocolloids which at least in theory are capable of being used in forming such bioreactor spheres or beads. In cases when an alginate is not employed in forming such structures it is considered that it is currently preferable to utilize various synthetic hydrocolloid or hydrocolloid type materials such as carboxymethylcellulose, methylethylcellulose, polyvinylalcohol and the like. In those instances where alginic acid is not used it is preferred to use such compositions rather than to substitute a naturally occuring hydrocolloid for the aliginic acid. It is believed that an understanding of this invention does not require a discussion as to all of the reasons why the latter is the case.

In any such bead it is important that the hydrocolloid or hydrocolloid type material used be "biocompatible" in the sense that such material will not interfere with and will be inert with respect to either the cells used or the enzymes associated with these cells. This latter is also considered to be important in connection with the selection of a particular substance(s) and/or ion(s) capable of reacting with the hydrocolloid used so as to form a membrane or skin as indicated in the preceding discussion. Obviously such a substance or ion should not interfere with either the cells or the enzymes associated with such cells. This type of factor has been especially important in precluding the use of compounds such as glutaraldehyde in treating cells or membranes in microbial beads or spheres so as to improve the strength characteristics of at least the films or membranes of such beads or spheres.

The comparative strength and/or resistance to disruption of such membranes or surface barriers in microbial spheres is quite important. This is because such spheres or beads are quite commonly handled in such ways that they are subjected to various physical forces which might tend to break them up or at least open up the skins on them to a sufficient extent as to preclude their intended use in a desired manner. Forces which will tend to break up such spheres or beads will be applied to them not only as they are handled, but in addition, frequently may be applied to them because of the manner in which a particular bioreactor is constructed and/or operated. Since bioreactors can be built and operated in a variety of different ways it is not considered necessary to specifically identify any particular bioreactor in this specification so as to show how forces can be applied to beads or spheres within it as it is being used.

As a result of the comparatively low strengths of the membranes or peripheral barriers in bioreactor beads or spheres as indicated causing such structures to tend to break or at least crack as they are handled or used it is considered that bioreactors requiring the use of such beads or spheres have not been widely adopted or utilized in many instances where such bioreactors might be advantageous because of the manner in which cells are immobilized and held within the beads and spheres of the type indicated in the preceding discussion. Thus, it is considered that in many instances the advantages growing out of or resulting from the use of bead or sphere like structures containing immobilized microbial cells have not been achieved because of the comparatively fragile character of such beads or spheres.

BRIEF SUMMARY

The invention set forth in this specification is intended to provide new and improved bead or sphere-like structures containing immobilized microbial cells which are more desirable than related structures indicated in the preceding discussion as a result of their having been manufactured in such a way as to be comparatively resistant to various types of physical forces which tend to cause prior microbial beads to rupture. An object of the present invention is to provide new and improved structures as indicated which may be easily and conveniently manufactured at a comparatively nominal cost and which are capable of being utilized effectively in a desired manner in various applications in which prior similar structures were not acceptable for comparatively long periods.

In accordance with this invention these various objectives are achieved by providing a microbial sphere or bead in which microbial cells are immobilized within the sphere or bead through the use of normally insoluble fluid impermeable membrane enclosing the bead in which the improvement comprises: said membrane including an amount of finely divided sericitic clay in an amount which is effective to improve the strength characteristics and the resistance to tearing of said membrane.

BRIEF DESCRIPTION OF THE DRAWING

Because of the nature of this intention it is best more fully described in the accompanying drawing in which:

the FIGURE illustrates the nature of the presently preferred bead or sphere containing immobilized microbial cells in accordance with this invention.

It is to be realized that the accompanying drawing is primarily intended for explanatory purposes. Thus it is not intended to illustrate any particular bead or sphere drawn to scale nor is it intended to indicate the relative dimensions between the membrane or skin in the structure and the diameter of the structure.

DETAILED DESCRIPTION

As indicated by the description of the drawing it shows a particular bead or sphere 10 which includes a peripheral skin or membrane 12 enclosing and holding a core 14. The core 14 normally will contain a solution of one or more hydrocolloids in an appropriate solvent—normally water—which is mixed with a loaded with microbial cells 18. On occasion some of these cells 18 will be located within and more or less caught up within the membrane 12. Normally a bead such as the bead 10 will be from about 2 to about 6 mm in diameter. If desired such a bead may be larger or smaller than this.

With the present invention both the solution 18 and the membrane 12 will contain an amount of finely divided sericitic clay particles 20 which is effective to improve the strength and tear resistance characteristics of the membrane 12. This clay is also advantageously used since it is a good absorbent for enzymes—especially lactose enzymes. Because of the extremely small sizes of the particles of the clay used these particles are merely indicated in the drawing by stippled dots. For convenience this numeral 20 is applied in the drawing to only a single particle as shown by a single stippled dot.

The bead 10 can be formed by simply varying the type of process as indicated in the preceding discussion by such a process so as to incorporate within the solution of the hydrocolloid used—normally an aqueous solution of a sodium alginate—an amount of finely divided sericitic clay particles which will be effective to accomplish the results indicated in the preceding. Since the amount of such particles which will be effective will vary somewhat in accordance with the fineness of such particles and in accordance with the precise hydrocolloid used, the concentration of the hydrocolloid solution, the cells used and the quantity of such cells within the solution it is difficult to give precise values as to the amounts of such particles which should be used in all cases.

In general the beads or spheres should contain an amount of the sericitic clay which is effective to increase the physical strength of a membrane or skin such as a membrane 12, but which is insufficient to weaken the strength of such an membrane 12. To a degree the amount should also be necessary to accomplish this type of result will also be related to the size of the particles. It is considered that to obtain effective results in accordance with the invention that the particles of the sericitic clay used should at least be $-100$ mesh standard Tyler Screen size and should preferably be $-325$ mesh standard Tyler Screen size. It is considered that normally a dry or solvent free composition used to create a bead or sphere 10 should contain at least 5% by weight of such particles if the result to be achieved with such invention are to be meaningful, but that the composition should preferably not contain more than about 40% by weight of such particles to avoid a detrimental physical effect.

These figures will vary somewhat depending upon the precise origin of the sericitic clay used. The sericitic clays referred to in this discussion are micaceous minerals which normally contain a small amount of montmorillonitic-type material. Normally the latter will not be a traditional or true montmorillonite because it does not have expansion characteristics on glycolation. The clays of the type preferably used with the invention are mined in the San Jacquin Valley in the State of California, USA and are centered in various towns such as Taft, McKittrick and others. A typical analysis of such a clay is as follows:

| | |
|---|---|
| Silica | 80.40% |
| Aluminum Oxide | 9.48% |
| Iron Oxide | 0.88% |
| Calcium Oxide | 0.20% |
| Magnesium Oxide | 0.54% |
| Sodium & Potassium Oxides | 0.15% |
| Loss on ignition (largely combined water) | 8.35% |
| | 100.00% |

It will, of course, be recognized that the composition of any such clay will vary somewhat depending upon where it is mined or upon its location within a deposit. The deposit from which the sample used for the foregoing analysis was obtained will not vary to such an extent as to contain greater than 10% more or less of any of the ingredients specified except water. In this particular type of sericitic clay some cristobalite will normally be present as an impurity. Further, this type of clay will normally contain a very limited amount of opaline quartz. Normally, sericitic clay as noted will contain from about 40 to about 60% by weight of an easily solubilized amorphous silica.

The use of an sericitic clay as indicated is preferable with the present invention because of its effectiveness in increasing the physical strength of the membrane. This effectiveness is considered to be an outgrowth of the adsorbent, absorbent properties of the clay. In general, the more finely divided the particles of the clay the greater the extent to which these properties are utilized in the final product. This is the result of the fact that a given weight of finely divided particles will possess a greater surface area than the equivalent weight of particles which are coarser than those finely divided ones.

The physical properties of the clay are important in that it is believed that they enable the clay to more or less "take up" a hydrocolloid such as the alginic acid mentioned in the preceding discussion in such a manner that the alginic acid is held by or holds to the particles as the alginic acid or other hydrocolloid is converted into an insoluble membrane by a process as indicated in the preceding discussion. For this result to be achieved an amount of the alginic acid or other hydrocolloid must be used which is effective in cooperation with the sericitic clay to create a physically strong, coherent membrane. The precise amount of a hydrocolloid used with a given amount of sericitic clay should preferably be determined on an emperical basis. Generally speaking satisfactory results can be anticipated when the amount by weight of the hydrocolloid is within the same range given relative to the amount of clay which can be used.

On a dry weight basis the remainder of any composition used to create a mixture useful in the production of a bead or sphere 10 will consist of the weight of the cells used within the beads or spheres. Generally speaking if effective results are to be achieved on a dry weight basis of a composition should contain from about 10 to about 40 parts per weight of dry cells. Obviously the greater the concentration of the cells the greater of the amount of enzymes present in a bead or sphere 10 for use in carrying out the desired reaction or transformation. On the other hand the use of an amount of cells in excess of an amount as specified will detrimentally physically effect the product obtained.

Such a composition as indicated will, of course, be mixed with a solvent—normally water—prior to beads or spheres 10 being formed in accordance with a conventional process. Since the latter are well established it is not considered it necessary to encumber this specification with a detailed description of them.

Normally, when alginic acid is used the mixture indicated in the preceding discussion will be passed from a dropper or through a screen into a bath containing calcium ions so as to render the alginate insoluble in order to create a skin or membrane. If the bath used is highly concentrated with the calcium ion or is significantly warm or if the beads created are left in this bath for a prolonged period after being formed there will be a tendency for the cores of such beads to become gelled. This will be particularly apparent adjacent to the membrane 12. This is considered undesirable in that it may tend to delay or impede the movement of a solution into and out of a sphere 10 through a membrane 12 in a bioreactor. Since the use of these spheres 10 in bioreactors is known it is not considered necessary to describe it in this specification.

I claim:

1. In a microbial sphere or bead the exterior of which is formed of an insoluble fluid membrane in which microbial cells are immobilized within the sphere or bead the improvement comprising:

said membrane including on a dry weight basis from about 10 to about 40% by weight of a hydrocolloid selected from the group consisting of alginic acid, carboxymethyl cellulose, methylethylcellulose and polyvinyl alcohol, from about 10 to about 40% by weight particles of a −100 mesh standard Tyler screen size of sericitic clay and from about 10 to about 40% by weight of said cells:

said sericitic clay being effective to improve the strength characteristics and the resistance to tearing of said membrane.

2. A microbial sphere or bead as claimed in claim 1 wherein:

said hydrocolloid is alginic acid.

3. A microbial sphere or bead as claimed in claim 1 wherein:

said particles are of a −325 mesh standard Tyler screen size.

4. A microbial sphere or bead as claimed in claim 3 wherein:

said hydrocolloid is alginic acid.

* * * * *